US010926063B2

(12) United States Patent
Cupelli et al.

(10) Patent No.: US 10,926,063 B2
(45) Date of Patent: Feb. 23, 2021

(54) DECOMPRESSION NEEDLE ASSEMBLY (71) Applicant: North American Rescue, LLC, Greer, SC (US)

(72) Inventors: Matt Cupelli, Greer, SC (US); Brent Bronson, Duncan, SC (US); Scott Bolleter, San Antonio, TX (US)

(73) Assignee: North American Rescue, LLC, Greer, SC (US)

( * ) Notice: Subject to any disclaimer, the term of this patent is extended or adjusted under 35 U.S.C. 154(b) by 0 days.

(21) Appl. No.: 15/046,056

(22) Filed: Feb. 17, 2016

(65) Prior Publication Data

US 2017/0232164 A1    Aug. 17, 2017

(51) Int. Cl.
*A61M 25/06* (2006.01)
*A61M 39/24* (2006.01)
*A61M 25/00* (2006.01)
*A61B 17/34* (2006.01)
*A61B 17/00* (2006.01)

(52) U.S. Cl.
CPC ......... *A61M 25/0606* (2013.01); *A61B 17/34* (2013.01); *A61B 17/3474* (2013.01); *A61M 25/0068* (2013.01); *A61M 25/06* (2013.01); *A61M 39/24* (2013.01); *A61B 2017/00809* (2013.01); *A61M 25/007* (2013.01); *A61M 25/0041* (2013.01); *A61M 25/0097* (2013.01); *A61M 25/0693* (2013.01); *A61M 2025/0008* (2013.01); *A61M 2205/581* (2013.01); *A61M 2205/583* (2013.01); *A61M 2205/586* (2013.01)

(58) Field of Classification Search
CPC ............... A61M 1/04; A61M 25/0068; A61M 25/0097; A61M 25/06; A61M 25/0606; A61M 25/0693; A61M 39/24; A61M 1/00; A61M 25/00; A61B 17/0469
See application file for complete search history.

(56) References Cited

U.S. PATENT DOCUMENTS

| | | | |
|---|---|---|---|
| 4,230,123 A | 10/1980 | Hawkins, Jr. | |
| 5,300,046 A * | 4/1994 | Scarfone | A61B 17/3496 251/149.8 |
| 5,356,386 A | 10/1994 | Goldberg et al. | |
| 5,478,333 A | 12/1995 | Asherman, Jr. | |
| 5,819,921 A * | 10/1998 | Schmid | A61C 19/02 206/210 |
| 6,217,556 B1 * | 4/2001 | Ellingson | A61B 10/0283 604/167.01 |
| 7,229,433 B2 | 6/2007 | Mullen | |
| D595,847 S | 7/2009 | Miller et al. | |
| 8,057,443 B2 | 11/2011 | McNeil | |

(Continued)

*Primary Examiner* — Kevin C Sirmons
*Assistant Examiner* — Tezita Z Watts
(74) *Attorney, Agent, or Firm* — Dority & Manning, P.A.

(57) ABSTRACT

The present invention is a decompression needle assembly having a needle that is removable received into to a catheter. The catheter can include a rigid portion and a deformable portion wherein the deformable portion can be multi-ported at its distal end. A one-way valve contained in a catheter hub attached to the catheter wherein the one way valve is in an open position when the needle is received in the catheter. Lateral catheter openings can be defined in the catheter and disposed adjacent to a distal end of the catheter. A plunger can be received within the needle and have an visual and auditory indicator that can be appreciated through the needle hub.

13 Claims, 5 Drawing Sheets

(56) References Cited

U.S. PATENT DOCUMENTS

| | | | | |
|---|---|---|---|---|
| 8,105,288 B2* | 1/2012 | Keyser | .................. | A61M 29/02 |
| | | | | 604/164.1 |
| 8,257,339 B1* | 9/2012 | Rosado | ................ | A61M 39/24 |
| | | | | 604/506 |
| 8,579,115 B2* | 11/2013 | Murphy | ................ | A61M 5/002 |
| | | | | 206/364 |
| 2006/0178635 A1* | 8/2006 | Callaway | .......... | A61M 25/0606 |
| | | | | 604/164.09 |
| 2007/0078442 A1* | 4/2007 | Mayse | .............. | A61M 25/0097 |
| | | | | 604/533 |
| 2008/0082053 A1* | 4/2008 | Carlyon | ............ | A61M 25/0606 |
| | | | | 604/168.01 |
| 2013/0178760 A1* | 7/2013 | Downie | ............. | A61B 5/15003 |
| | | | | 600/579 |
| 2013/0310750 A1* | 11/2013 | Hopman | ............... | A61M 1/008 |
| | | | | 604/159 |
| 2014/0207069 A1* | 7/2014 | Bierman | ............... | A61M 25/06 |
| | | | | 604/167.03 |
| 2014/0221932 A1* | 8/2014 | Puhasmagi | ....... | A61M 25/0097 |
| | | | | 604/167.05 |

* cited by examiner

DECOMPRESSION NEEDLE ASSEMBLY

BACKGROUND OF THE INVENTION

1. Field of the Invention

This invention is directed to a decompression needle assembly with improved features for treating tension pneumothorax, and pneumothorax especially by first responders and providers of emergency and critical care medicine.

2. Description of the Related Art

There remains a dedicated focus on mitigating major preventable causes of death in combat and civilian situations. These causes consist of, but are not limited to, compressible hemorrhage, traumatic airway obstruction and tension pneumothorax. This focus results from the expressed need to address such preventable deaths. One such cause, tension pneumothorax, while relatively rare in civilian settings, is a leading cause of preventable death on the modern battlefield. It also remains a concern in the civilian setting. Tension pneumothorax can result from penetrating chest trauma as seen on the battlefield, motor vehicle collision, or mass shooting, for example. Without treatment, tension pneumothorax rapidly progresses to shock and death, and the emergency treatment of choice is needle decompression.

Tension pneumothorax is the progressive build-up of air within the pleural space, usually the result of a laceration of the lung which allows air to escape into the pleural space, with the subsequent building of pressure, preventing the lung from inflating and ultimately causing the lung to collapse. Tension pneumothrox also can be caused by penetrating trauma if the resulting defect in the chest wall allows air to enter the pleural space but not escape. Progressive build-up of pressure in the pleural space pushes the mediastinum to the opposing hemithorax, and may obstruct venous return, and adequate filing of the heart. This condition often leads to circulatory instability and may result in traumatic arrest.

On study as reported in The Journal of Trauma Injury, Infection, and Critical Care, found that of the 978 casualties that were studied, 55 died solely from tension pneumothorax. This number potentially represents a 5% to 6% preventable fatality rate. Therefore, tension pneumothorax is condition that when properly managed can results in a significant number of lives saved.

Historically, the management of tension pneumothorax involves emergent chest decompression with needle thoracotomy. However, this treatment is not without risks. Needle thoracotomies have several potential complications that include blockage of the canulla (needle) or catheter, kinking of the catheter, or damage to the lung if the distal end of the catheter contacts the lung as the lung re-inflates. It is further noted that if the catheter is blocked as the lung re-inflates, the relieved tension may re-accumulate undetected.

In order to minimize these complications, it would be advantageous to have a decompression needle and catheter assembly that had improved insertion characteristics, reduced or eliminated blockage, and limited or prevented kinkingof the catheter or damage to the lung. Also, it would be advantageous to have a decompression needle and catheter assembly that prevents negative pressure in the pleural space from drawing fluid into the pleural space through the catheter.

One such design is the ARS for Needle Decompression offered by North American Rescue, LLC the Applicant that includes a 14 gauge needle that is about 3.25 inches long and received in a catheter, the casing shown in U.S. Design Pat. No. D595,847. The design includes a needle inserted into a catheter so that the needle and catheter are inserted into the patient and when the catheter tip is positioned in the pleural space, the needle is removed.

A noted issue occurs when inserting the decompression device. The provider may grasp the needle and catheter assembly and by grasping only the catheter, disadvantageously cause the needle to retract into the catheter prior to proper insertion. This can prevent the needle and catheter from being properly inserted. It would be advantageous to have an assembly where the needle and catheter can be temporarily attached to each prior to the assembly being inserted into the patient.

Some attempts to improve the needle and catheter combination include U.S. Pat. No. 4,230,123 that discloses a small gauge needle which is comprised of a stylus within a cannula. The invention includes means for locking the cannula of the small gauge needle to the stylus. However, this design includes a cap on one end of the stylus that provides means for locking the stylus to the probe cannula preventing fluid from escaping unless the cap is removed. U.S. Pat. No. 5,478,333 discloses a medical dressing that includes a one-way valve disposed to the exterior of cylindrical section of duct segment by an adhesive material that is capable of being sterilized. The invention is designed to be used with a decompression needle and to be applied after the needle is inserted.

U.S. Pat. No. 7,229,433 discloses a catheter assembly comprised of a tube dimensioned to receive the stylet and a hub integrally attached to the distal end of the catheter assembly for receiving the stopper. The one-way valve composed of a pliable material covers the hub. The lumen of the one-way valve is continuous with the lumens of the tube and the hub of the catheter assembly. This invention is not suited for the dynamic/austere setting and required the one-way valve to be attached to the hub.

U.S. Pat. No. 8,057,443 discloses a port in fluid communication with the atmosphere; a catheter having a proximal end arranged to be inserted into the body of an individual and having a distal end; a one-way valve; and a fluid passage switch reversibly movable between a first position in which the distal end of the catheter is in fluid communication with the port and a second position in which the distal end of the catheter is in fluid communication with the one-way valve, the one-way valve being arranged to permit fluid flow there through in a direction from the distal end of the catheter. However, this design requires that the valve be arranged in a certain position to allow the one-way valve to operate. A similar disadvantage exists with the design of U.S. Pat. No. 6,217,556.

Further, these designs, including that of U.S. Pat. No. 5,356,386 are not well suited for the dynamic/austere setting in that they are not designed to account for the provider's reaction to tachypsychia, the fight or flight response. In the dynamic/austere setting, the provider can be significantly affected by high stress, reaction to a violent situation, and other conditions. The reaction to these conditions can results in tunnel vision, auditory exclusion, the loss of fine and complex motor control, irrational behavior, and the inability to think clearly. Therefore, medical devices that require fine motor skills or thought processes or operational procedures are disadvantages to the provider in the dynamic/austere setting. Additionally, unnecessarily complex packaging can be a significant disadvantage in the dynamic/austere setting. Ideally, what works in the operating room or emergency department of a hospital may not work in the dynamic/austere setting. This problem is often the result of device design limitations, staff availability for device assembly and a lack of packaging restrictions.

It would be advantageous to have a decompression needle assembly designed for the dynamic/austere setting that would minimize these disadvantages and be able to be stored in a package that was light weight and compact for transportation as the provider generally carries the needed supplies. For example, in the combat or law enforcement setting having a decompression needle that can be carried by each person engaged would allow the provider to use the injured person's supplies without having to carry multiple devices.

It is an object of the present invention to provide for a decompression needle assembly that mitigates blockage of the catheter, provides for temporary locking of the catheter to the needle without blocking the fluid flow, prevent the catheter from damaging the lung when the lung inflates and prevents reverse fluid flow into the pleural space when the catheter is in position.

It is another object of the present invention to provide for a needle and catheter assembly that cooperates with the packaging so that the assembly can be more easily used by a provider that experiences the effects of tachypsychia.

BRIEF SUMMARY OF THE INVENTION

The above objectives are accomplished by providing a decompression needle assembly comprising: a housing having a removable housing cap; a catheter having a catheter hub; a temporary lock tab attached to a rear portion of the catheter hub; a rear catheter opening defined in the catheter hub; a one-way valve attached within the catheter hub; a needle received in the catheter and extending through the one way valve placing the one way valve in an open position; a needle hub attached to the needle having a temporary lock collar, rotatable and fixed to the needle hub for engaging and disengaging secure the needle hub to the catheter hub; a needle hub extension configured to be received in rear catheter hub opening when the needle hub is attached to the catheter hub; and, a storage position wherein the needle and catheter assembly are attached and received in a housing so that the catheter hub is received in the housing and the lock collar extends from the housing.

The invention can include threads defined in the lock collar on an interior side and configured to temporarily engage and disengage with the lock tab. Catheter ridges can be included in the catheter hub representative of an annular ring. A semi-flexible curve or "pig-tail" can be included at the distal end of the catheter. Lateral openings can be defined in the catheter and disposed adjacent to the distal end of the catheter. A flash chamber can be defined by the cannula hub and lock collar. The cannula hub can be transparent. The lock collar can be transparent.

The catheter can have a straight position when the needle is received on the catheter and a semi-flexible, "pig-tail", or curved position when the cannula is removed from the catheter. The catheter can include a rigid portion and a deformable portion wherein the deformable portion is exposed at the catheter distal end. The invention can include a first flow path that extends from the distal end of the needle, through the needle, and out of the needle hub when the needle is received on the catheter; and, a second flow path that extends from the distal end of the catheter, through the one-way valve and our of the catheter hub when the needle is removed from the catheter.

The invention can include a one-way valve having a first open position when the needle is received on the one-way valve, and a second open position when slight pressure from the distal end of the catheter opens the one-way valve and a closed position when negative pressure in the pleural space attempts to draw air/fluid through the catheter into the pleural space.

BRIEF DESCRIPTION OF THE SEVERAL VIEWS OF THE DRAWINGS

The details of the present invention, both as to its structure and operation, are understood in part by study of the accompanying drawings which are referenced herein and in which like reference numerals refer to like parts and where.

DETAILED DESCRIPTION OF THE INVENTION

Figure 1:
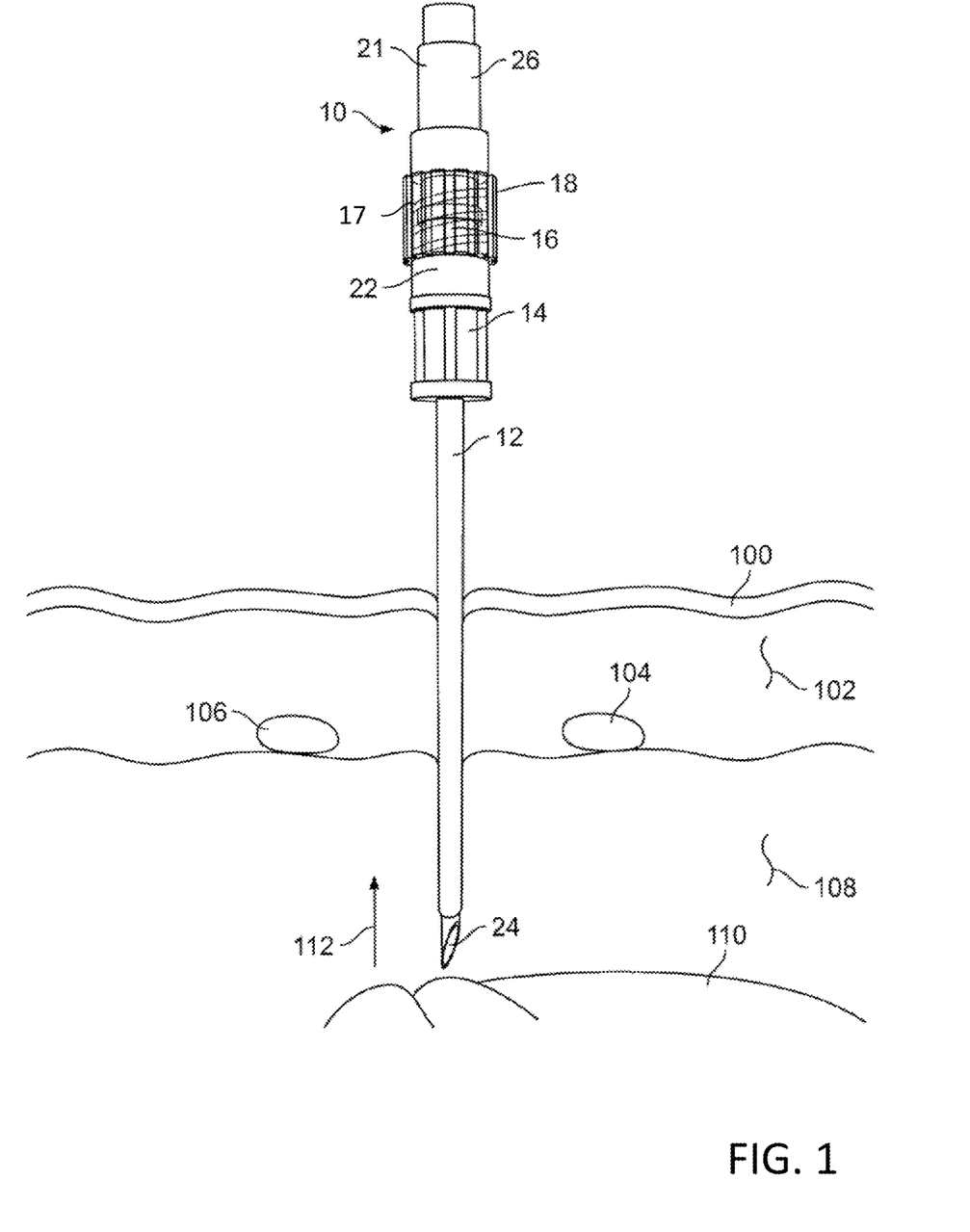
FIG. 1 is a side view of aspects of the invention.

Referring to FIG. 1, the decompression needle assembly 10 including a catheter 12 that has an outward flow path defined from the distal end of the catheter to the proximal end of the catheter. The catheter hub 14 is attached to proximal end of the catheter. A rear portion 16 of the catheter hub can be attached to the catheter hub or included in the catheter hub. The rear portion of the catheter hub include one or more lock tabs 20 (FIG. 3) that extends laterally from the catheter hub perpendicular to the outward flow path. A one-way valve 22 is disposed within the catheter hub and opens when pressure is applied along the flow path and prevents fluid flow in a direction opposite the flow path.

A needle 24 can be received in the catheter from the proximal end and pass through the one-way valve and extend from the distal end of the catheter. The needle can include a needle hub 26 that includes a flash chamber 21 to assist in indicating when the needle has been properly inserted into a patient. This indication may be auditory (such as a click) or visual. A lock collar 18 can be included in the catheter hub and attached to the forward portion of the catheter hub adjacent to the catheter when the catheter and cannula are assembled. In one embodiment, the temporary lock collar can rotate about needle hub and engage the lock tabs to attach or disarticulate the needle hub to or from the catheter hub. The lock collar can include internal threads 17 that engage or disengage the tabs to secure or release the needle to or from the catheter.

In the manufacturer of the assembly, the needle can extend through the one-way valve positioning the one-way valve in an open position. When the needle is removed from the catheter, the one-way valve closes and only opens when fluid flow is in the direction of the fluid flow path. As such, the needle cannot be re-inserted into the catheter, providing additional safety against contamination and mitigating further injury to the patient.

In operation, the needle and catheter assembly is removed from the housing and inserted into the patient. The needle and catheter are inserted into the skin 100, through an area 102 below the skin 100, and between ribs 104 and 106 until the assembly enters the pleural space 108. In one embodiment, depth markings or color coding, along the length of the catheter, can assist the provider with the depth recognition and procedural safety during the insertion process. Intra-thoracic pressure can be relieved from the pleural space before the needle is removed. The needle is removed, leaving the catheter in position, and the lung 110 may begin to re-inflate once pressure in the pleural space is relieved and begins to travel in direction 112.

Figure 2:
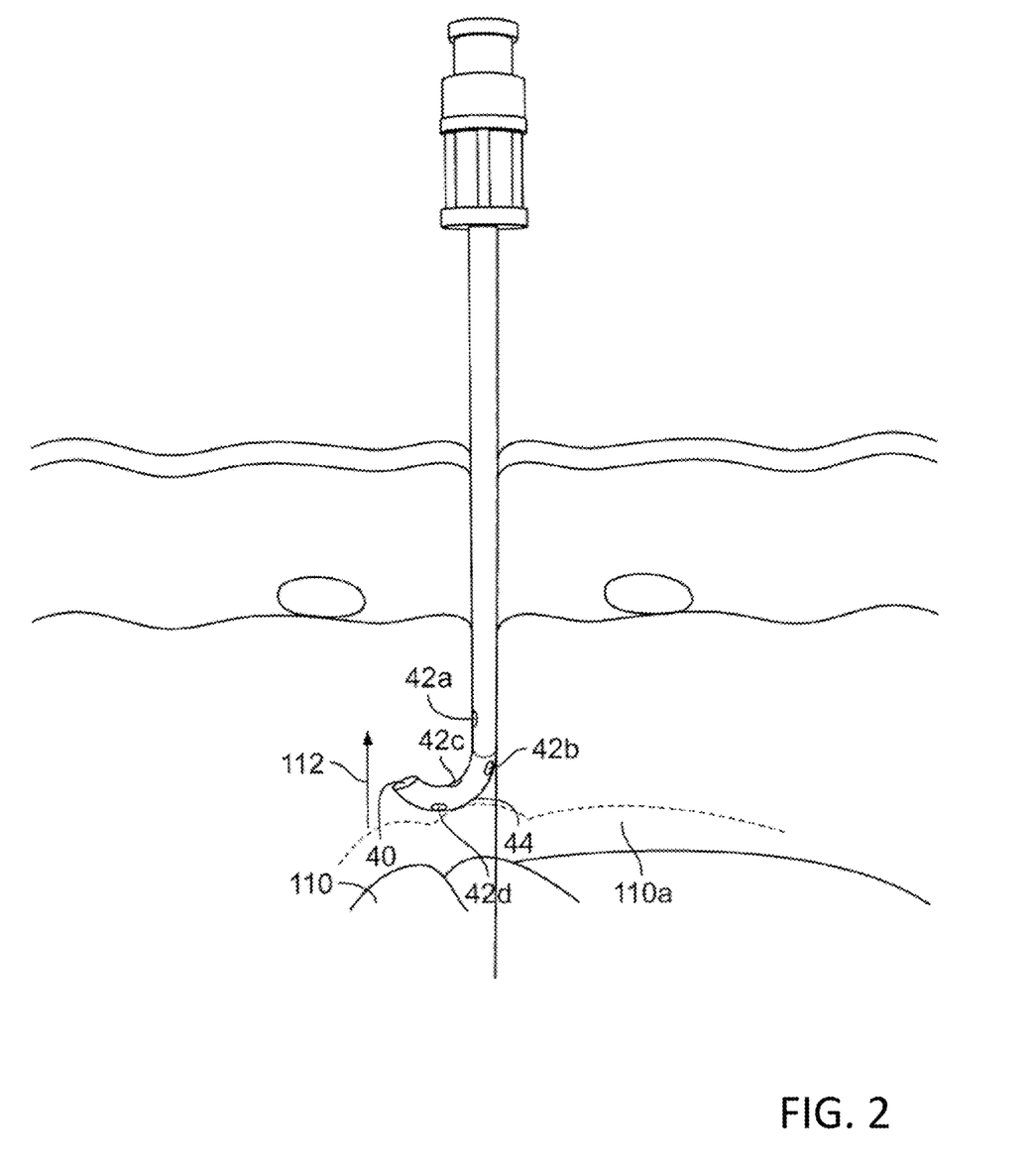
FIG. 2 is a side view of aspects of the invention.

Referring to FIG. 2, the catheter is shown once the needle is removed. Distal end of the catheter 40 is shown in the pleural space. As the lung begins to inflate and expand into a direction shown as 112. In one embodiment, the distal end of the catheter includes a semi-flexible curve or "pig-tail" 44 such that the distal end of the catheter curves away from the lung. When the lung inflates and expands in direction 112, the lung can contact the curved portion causing the distal end of the catheter to further flex away from the lung preventing the catheter's distal opening from being blocked by the expanding lung. Additionally, the lateral openings 42a through 42d can be included near the distal end of the catheter to allow fluid to travel along the flow path even if the catheter's distal opening is obstructed. When the needle is received by the catheter, the catheter is straightened by the needle allowing the catheter to be inserted into the patient, and to be received into and stored in its housing.

In one embodiment, the flash chamber is transparent to allow for fluid to be seen when the needle is properly placed in the pleural space. Continuity between the distal and proximal ends further allows for an auditory indication of proper placement. In one embodiment, the lock collar is also transparent to allow for fluid to be seen when the needle is properly placed on the pleural space.

Figure 3:
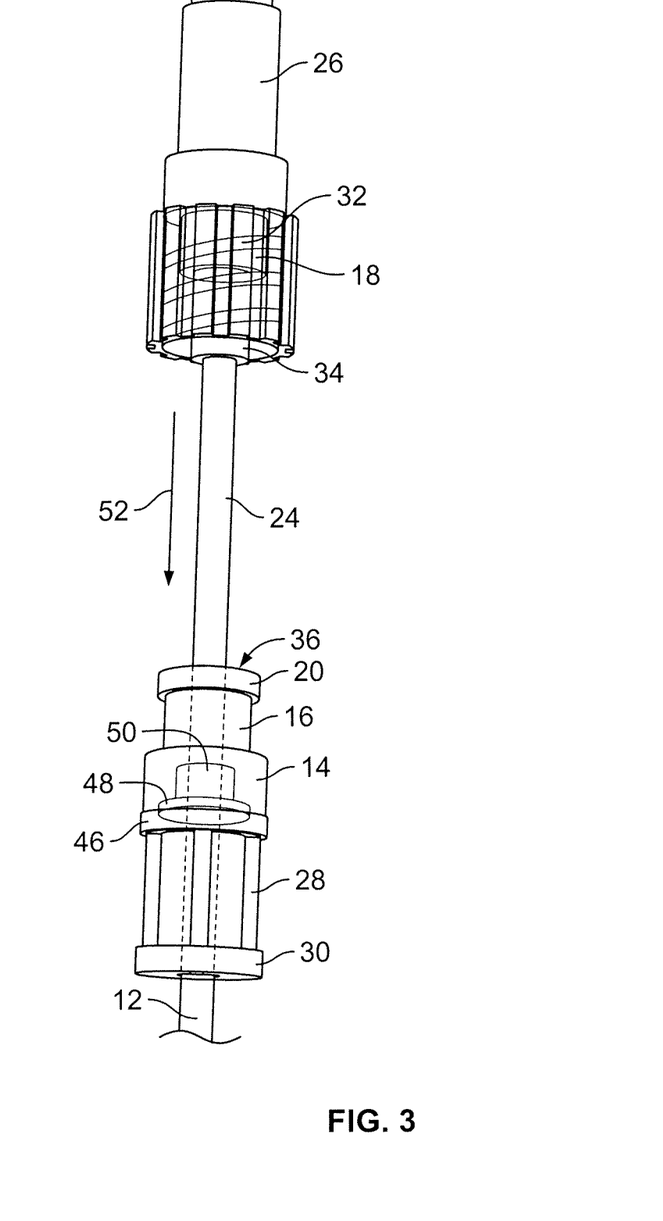
FIG. 3 is a side view of aspects of the invention.

Referring to FIG. 3, the needle hub can include a needle hub extension 34 that can be received in the rear of the catheter hub 36. The catheter hub can include ridges 28 to assist with grasping the catheter hub. A catheter hub annular ring 30 can be included in the catheter hub to assist with grasping and inserting the assembly. A one-way valve portion 46 of the catheter hub can include the one-way valve. The one-way valve is held in the open position by the needle when the needle extends through the one-way valve. When the needle is removed, valve 50 closes preventing air/fluid from flowing in a direction shown as 52. The one-way valve can be secured by the valve base 48 that is secured to the one-way valve portion of the catheter hub.

In one embodiment, the needle hub 26 includes a bore extending through the needle hub and is in fluid communications with the bore of the needle allowing fluid to travel from the distal end of the needle to the needle hub. A semi-porous audio cap can be attached to the needle hub to enhance insertion recognition at the proximal end of the needle hub.

Figure 4:
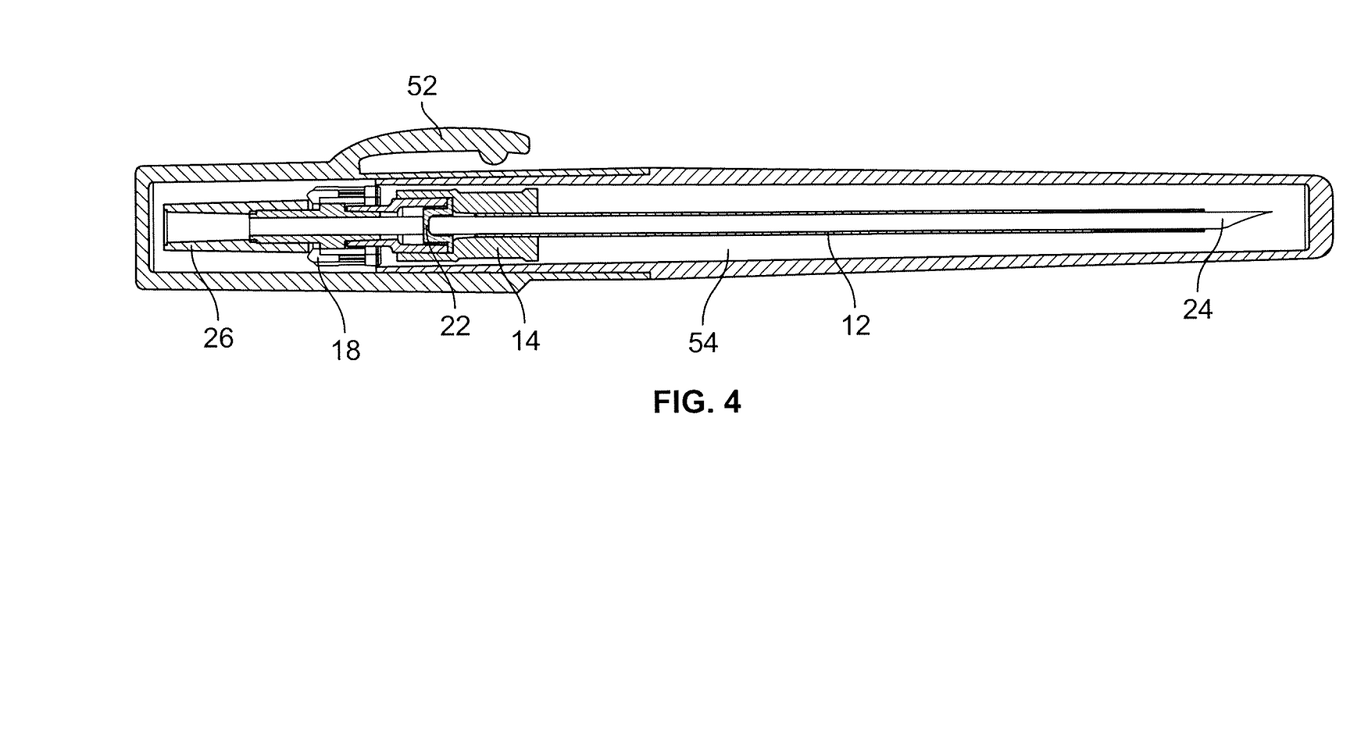
FIG. 4 is a side view of aspects of the invention; and,
FIG. 5 is a side view of aspects of the invention.

Referring to FIG. 4, the decompression needle assembly is shown received in housing 54 and covered by housing cap 52. In one embodiment, the one way valve portion 22 is received into the housing providing additional protection to the one-way valve. The lock collar and needle hub extend above the housing when the decompression needle assemble is received in the housing and the housing cap is removed. In one embodiment, the locking collar is received on the housing to provide additional protection to the lock collar. When the needle hub is pulled away from the housing, with the housing cap removed, the lock collar facilitates the catheter hub resulting in the catheter hub and catheter being removed from the housing as well. By having an in-line one way valve, catheter hub locked to a needle hub, straightened distal end of the catheter, the decompression needle assembly can be stored in a single, all-inclusive, and compact configuration allowing many units to be carried by a first responder. Additionally, the operator, such as law enforcement, a war fighter, or fireman can carry one unit usable by the provider to treat a tension pneumothorax without the addition of unacceptable weight or bulk to the provider or operator's equipment. By having the housing and housing cap designed as shown with the decompression needle assembly stored as described, the first responder or provider can quickly remove the housing cap and remove the decompression needle assembly without reliance on fine motor skills.

Figure 5:
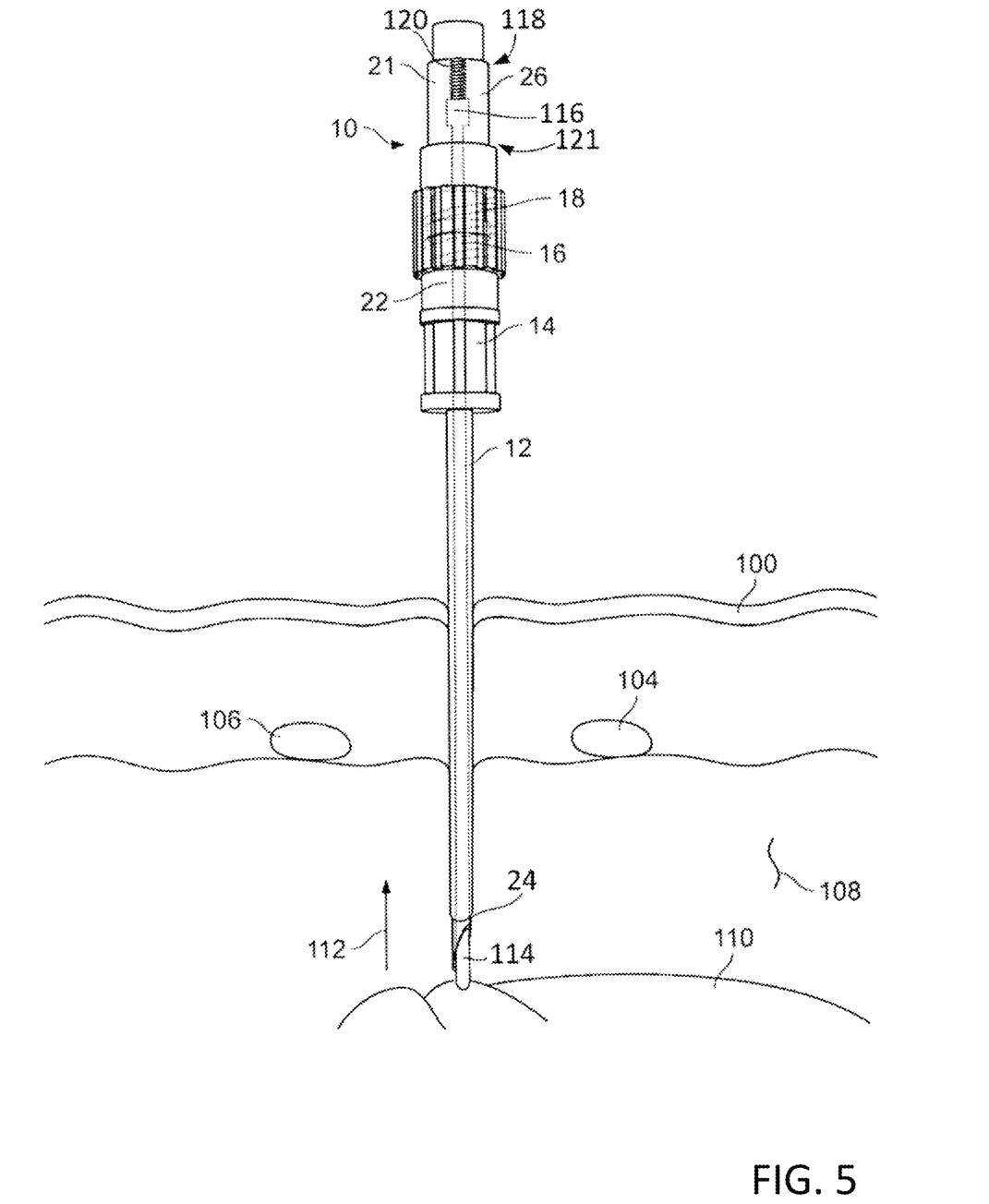

Referring to FIG. 5, one embodiment is shown with the a safety indicator for assisting with insertion of the needle and catheter assembly 24 to the proper depth. A plunger 114 is received into the needle and can extend into the needle hub 26. The plunger can be hollow in one embodiment. The needle hub can be transparent so that the depth indicator 116 can be seen through the needle hub. When the needle is inserted into the patient, the indicator (colored in one embodiment) is initially positioned to the top of the needle hub in area 118. This results from the plunger being pressed upward toward the needle hub when the plunger contacts the skin. When the needle enters the pleural space above the lung, the plunger returns to its resting position. This results in movement of the indicator and can produce an auditory "click", biased by spring 120, which has return to an area at the bottom of the needle hub shown as 122. If the plunger contacts the lung, the plunger is forced upwards and the indicator also moves upward indicating that the downward force on the needle should be halted. Once the assembly is properly inserted, the needle can be removed thereby leaving the catheter and creating a flow path for fluid from the pleural space to the environment allowing the pressure in the pleural space to be relieved. Therefore, the described indicator can assist the provider with insertion and possibly prevent improper insertion of the needle set subsequently damaging the lung tissue.

While the invention has been described in connection with a preferred embodiment, it is not intended to limit the scope of the invention to the particular form set forth, but on the contrary, it is intended to cover such alternatives, modifications, and equivalents as may be included within the spirit and scope of the invention as defined by the appended claims.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

What is claimed is:

1. A decompression needle assembly comprising:
   a housing having a housing cap removably attached to said housing for receiving a needle hub;
   a catheter having a catheter hub disposed at a proximal end of said catheter;
   a lock tab attached to a rear portion of said catheter hub;
   a rear catheter opening defined in said catheter hub;

a needle having a distal end and a proximal end that is attached to said needle hub;

a one-way valve included in said catheter hub at a one-way valve portion of said catheter hub, wherein said one-way valve is in a first open position when said needle is received in said catheter and when said needle is removed from said catheter, said one-way valve closes and is configured to move from the first open position and prevent the reinsertion of said needle into said catheter;

a lock collar rotatably attached to said needle hub for engaging with the lock tab to secure said needle hub to said catheter hub;

a needle hub extension configured to be received in said rear catheter opening when said needle hub is attached to said catheter hub; and a storage position wherein said needle and said catheter are attached and received in said housing so that said catheter hub and said needle hub are received in said housing and said lock collar extends from the housing when said housing cap is removed from said housing, wherein the distal end of said needle is received in said catheter and extends through said one-way valve in the first open position, wherein said one-way valve includes a second open position wherein said needle is removed from said catheter permitting fluid through a distal end of said catheter and allowing fluid exiting said one-way valve to flow proximally and linearly through said one-way valve from said rear catheter opening, and wherein said one-way valve includes a closed position preventing fluid from flowing distally through said catheter.

2. The assembly of claim 1 including threads defined in said lock collar on an interior side and configured to engage with said lock tab.

3. The assembly of claim 1 including catheter ridges included in said catheter hub.

4. The assembly of claim 1 including a catheter annular ring included in said catheter hub.

5. The assembly of claim 1 including a curve at the distal end of said catheter.

6. The assembly of claim 5 further comprising a plurality of openings defined in said curve formed in the distal end of said catheter and arranged such that said plurality of openings extend along the length of said catheter.

7. The assembly of claim 1 including lateral openings defined in said catheter and disposed adjacent to the distal end of said catheter.

8. The assembly of claim 1 including a flash chamber defined by said needle hub and said lock collar.

9. The assembly of claim 1 wherein said needle hub is transparent.

10. The assembly of claim 1 wherein said lock collar is transparent.

11. The assembly of claim 1 wherein said catheter includes a rigid portion and a deformable portion wherein the deformable portion is disposed at a curve formed at the distal end of said catheter.

12. The assembly of claim 1 including:
a first flow path that extends from the distal end of said needle, through said needle, and out of said needle hub when said needle is received by said catheter so that fluid from inside a patient's pleural space may enter the distal end of said needle, travel through said needle and exit through said needle hub; and
a second flow path that extends from the distal end of said catheter, through said one-way valve and out of said catheter hub when said needle is removed from said catheter so that fluid from inside the patient's pleural space may enter the distal end of said catheter, travel through said catheter and said one-way valve and exit through said catheter hub.

13. The assembly of claim 1 further comprising a safety plunger having a proximal end that is spring biased to an upper portion of said needle hub and a distal end that extends through said needle and past the distal end of said needle so that when said needle is being inserted into a patient's skin, said proximal end of said safety plunger will be adjacent to said upper portion of said needle hub until said distal end of said needle enters the patient's pleural space, thus causing the proximal end of said safety plunger to move away from said upper portion of said needle hub and towards said distal end of said needle.

* * * * *